(12) United States Patent
Inadama

(10) Patent No.: US 6,319,202 B1
(45) Date of Patent: Nov. 20, 2001

(54) MEDICAL IMAGING METHOD AND APPARATUS AND ULTRASONIC IMAGING METHOD AND APPARATUS

(75) Inventor: Mitsuyoshi Inadama, Tokyo (JP)

(73) Assignee: GE Yokogawa Medical Systems, Limited, Tokyo (JP)

(*) Notice: Subject to any disclaimer, the term of this patent is extended or adjusted under 35 U.S.C. 154(b) by 0 days.

(21) Appl. No.: 09/501,020

(22) Filed: Feb. 9, 2000

(30) Foreign Application Priority Data

Apr. 14, 1999 (JP) .................................................. 11-106143

(51) Int. Cl.$^7$ ........................................................ A61B 8/00
(52) U.S. Cl. ............................................................ 600/437
(58) Field of Search ........................... 600/437, 440–447, 600/455, 459, 534; 348/163; 73/597, 625; 128/916; 367/7, 11, 130

(56) References Cited

U.S. PATENT DOCUMENTS

| 5,553,620 | * | 9/1996 | Snider et al. | 600/440 |
| 5,724,985 | * | 3/1998 | Snell et al. | 128/697 |
| 5,891,035 | | 4/1999 | Wood et al. | |
| 6,063,030 | * | 5/2000 | Vara et al. | 600/437 |

* cited by examiner

Primary Examiner—Marvin M. Lateef
Assistant Examiner—Ali M. Imam
(74) Attorney, Agent, or Firm—Moonray Kojima

(57) ABSTRACT

In order to provide a medical imaging method and apparatus and ultrasonic imaging method and apparatus in which the utility for a user is improved, a display area 904 open to the user is provided in the display screen for the medical image 902, and an external input image is displayed in the display area 904.

8 Claims, 6 Drawing Sheets

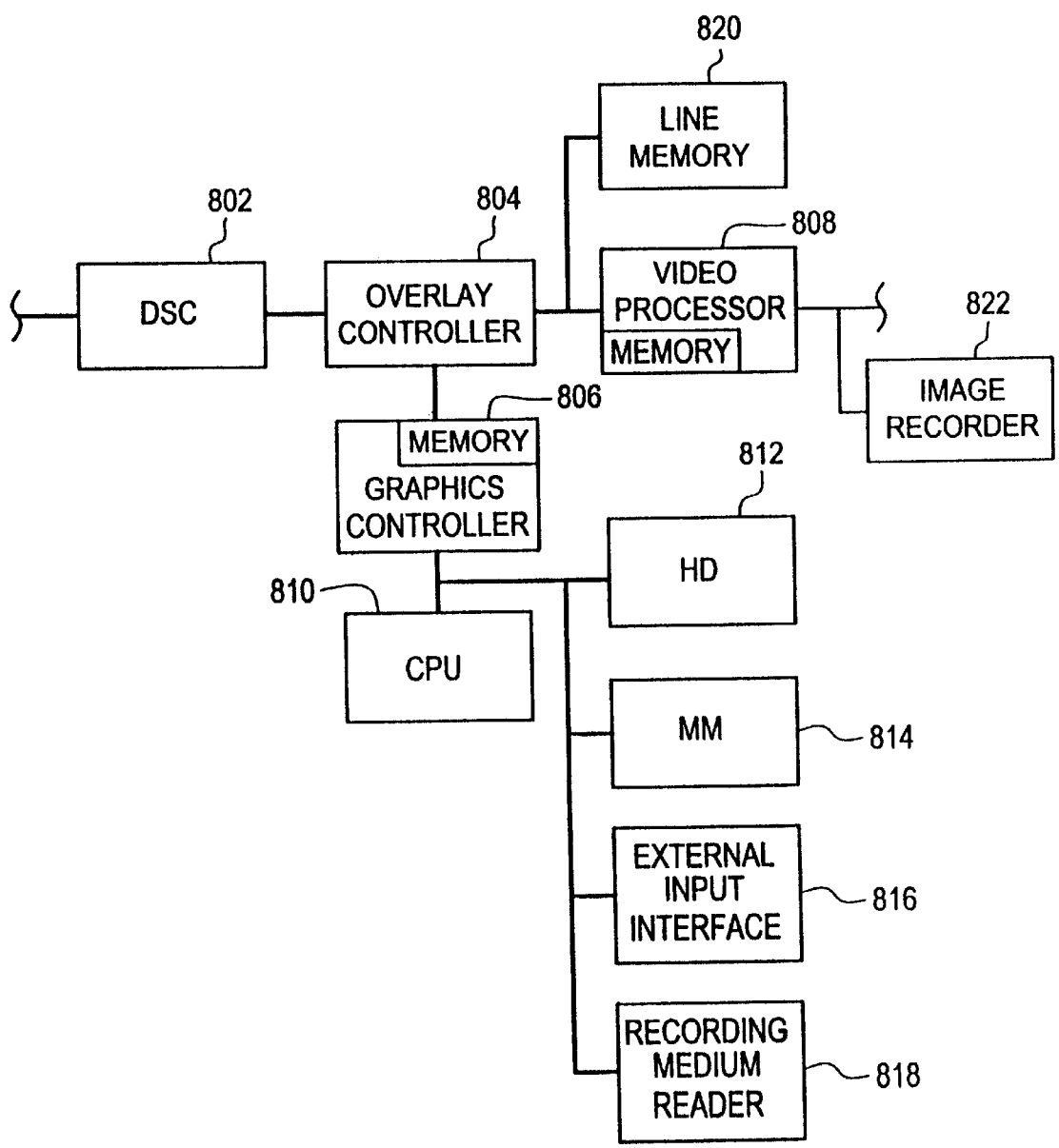

MEDICAL IMAGING METHOD AND APPARATUS AND ULTRASONIC IMAGING METHOD AND APPARATUS

BACKGROUND OF THE INVENTION

The present invention relates to a medical imaging method and apparatus and ultrasonic imaging method and apparatus, and more particularly to a medical imaging method and apparatus and ultrasonic imaging method and apparatus for collecting imaging data from a subject to be examined and displaying an image produced using the data.

An ultrasonic imaging apparatus transmits ultrasound to a subject, receives echoes of the ultrasound, produces an image based on the received echo signals, and displays the produced image to aid in diagnosis. The display of image is carried out by a display device such as a graphics display.

In the conventional display device for the ultrasonic imaging apparatus, a display area and images or character information to be displayed in the display area are predetermined by a manufacturer of the apparatus, and there is no area which can be freely used by a user, resulting in inconvenience in use.

SUMMARY OF THE INVENTION

It is therefore an object of the present invention to provide a medical imaging method and apparatus and ultrasonic imaging method and apparatus in which the utility for a user is improved.

In accordance with a first aspect of the present invention, there is provided a medical imaging method comprising the steps of collecting imaging data from a subject, producing an image based on the collected data, and displaying the produced image, wherein a display area open to a user is provided in a screen for the display.

In accordance with a second aspect of the present invention, there is provided a medical imaging apparatus comprising: data collecting means for collecting imaging data from a subject; image producing means for producing an image based on the collected data; and image display means for displaying the produced image, wherein the image display means has a display area open to a user in its display screen.

In accordance with a third aspect of the present invention, there is provided an ultrasonic imaging method comprising the steps of transmitting ultrasound, generating a received signal associated with the transmitted ultrasound, producing an image based on the generated received signal, and displaying the produced image, wherein a display area open to a user is provided in a screen for the display.

In accordance with a fourth aspect of the present invention, there is provided an ultrasonic imaging apparatus comprising: ultrasound transmitting means for transmitting ultrasound; received signal generating means for generating a received signal associated with the transmitted ultrasound; image producing means for producing an image based on the generated received signal; and image display means for displaying the produced image, wherein the image display means has a display area open to a user in its display screen.

(EFFECT)

According to the present invention, since a display area open to a user is provided in the display screen, the user can use the display area for any purpose and the utility of the apparatus is improved.

Therefore, the present invention can provide a medical imaging method and apparatus and ultrasonic imaging method and apparatus in which the utility for a user is improved.

Further objects and advantages of the present invention will be apparent from the following description of the preferred embodiments of the invention as illustrated in the accompanying drawings.

BRIEF DESCRIPTION OF THE DRAWINGS

FIG. 6 is a block diagram of a main portion of a data processing section in the apparatus shown in FIG. 1.

DETAILED DESCRIPTION OF THE INVENTION

Figure 1:
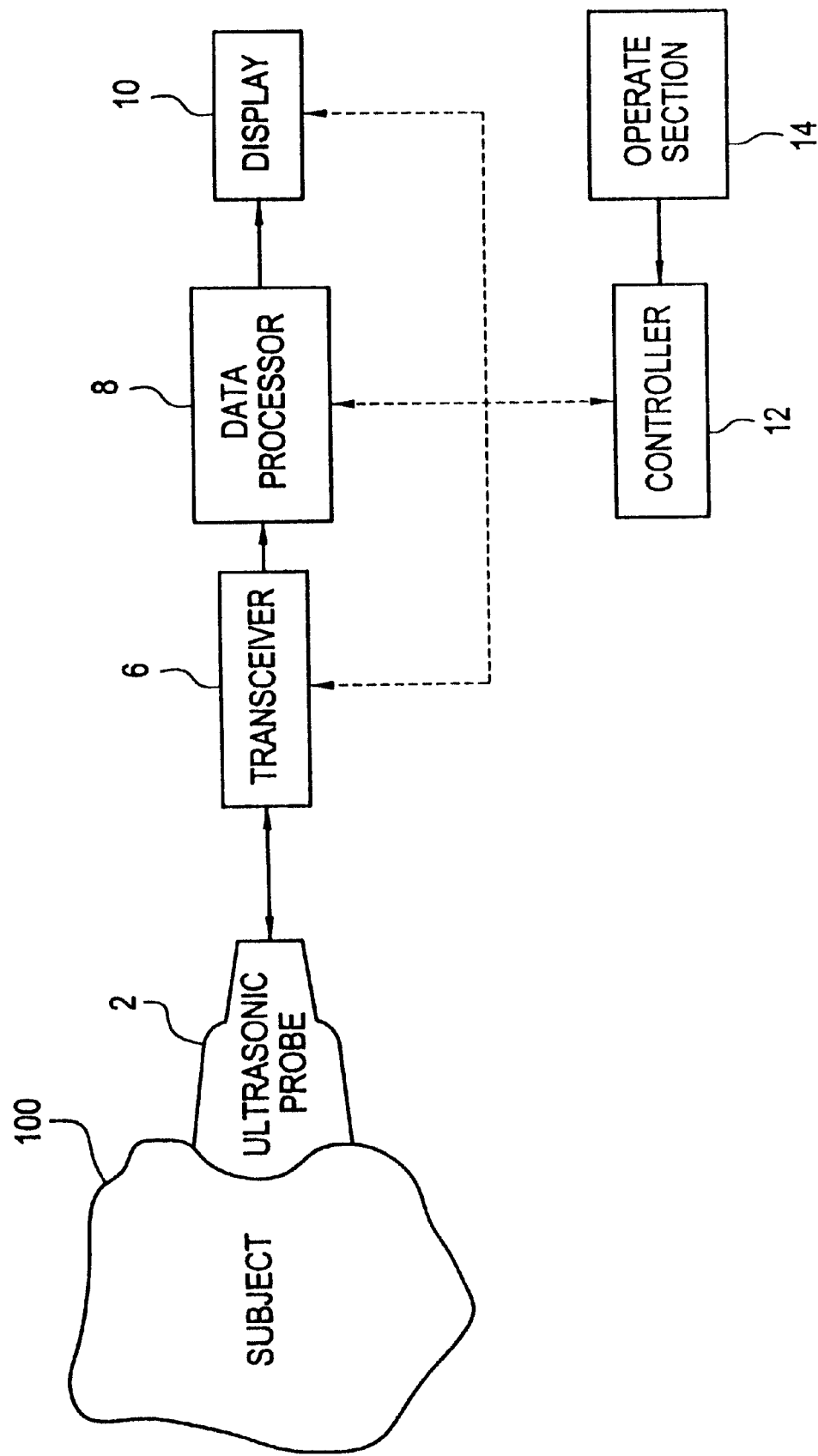
FIG. 1 is a block diagram of an apparatus in accordance with an embodiment of the present invention.

The embodiments of the present invention will now be described in more detail with reference to the accompanying drawings. FIG. 1 shows a block diagram of an ultrasonic imaging apparatus, which is an embodiment of the medical imaging apparatus of the present invention, and also is an embodiment of the ultrasonic imaging apparatus of the present invention. The configuration of the apparatus represents an embodiment of the apparatus in accordance with the present invention, and the operation of the apparatus represents an embodiment of the method in accordance with the present invention.

The configuration of the apparatus will now be described. As shown in FIG. 1, the present apparatus has an ultrasonic probe 2 for use in ultrasound transmission and reception abutting against a subject 100. The ultrasonic probe 2 has an ultrasonic transducer array (not shown) comprised of a plurality of ultrasonic transducers. The individual ultrasonic transducers are made from a piezoelectric material such as PZT (lead zirconate titanate [Pb—Zr—Ti]) ceramic.

Figure 2:
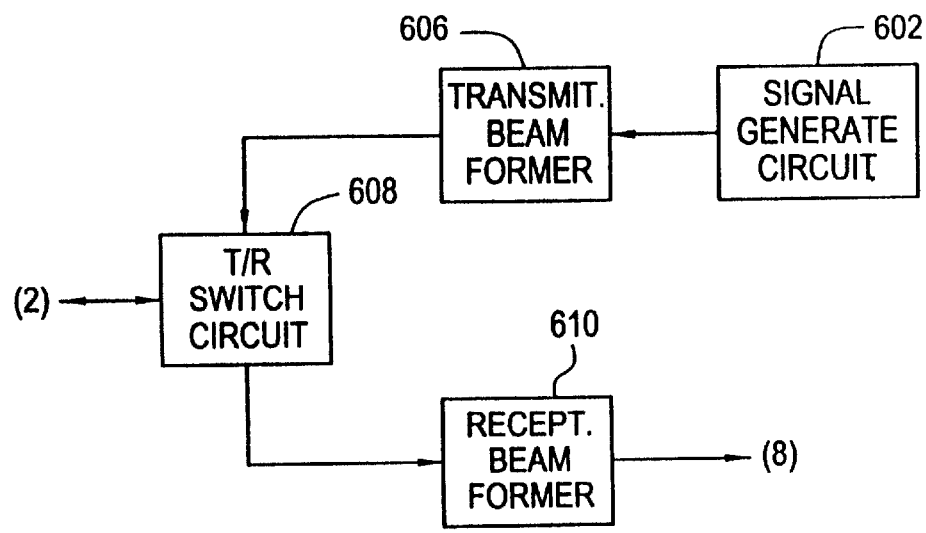
FIG. 2 is a block diagram of a transceiver section in the apparatus shown in FIG. 1.

The ultrasonic probe 2 is connected to a transceiver section 6 for driving the ultrasonic transducer array of the ultrasonic probe 2 to transmit an ultrasonic beam and receive echoes caught by the array. FIG. 2 shows a block diagram of the transceiver section 6. As shown, the transceiver section 6 has a signal generating circuit 602. The signal generating circuit 602 repeatedly generates pulse signals in a predetermined cycle, and inputs the signals to a transmission beamformer 606. The transmission beamformer 606 generates transmission beamforming signals based on the input signals. The transmission beamforming signals are a plurality of pulse signals to be supplied to a plurality of ultrasonic transducers that constitute a transmission aperture in the ultrasonic transducer array. The individual pulse signals are given respective delay times corresponding to the direction and focus of the ultrasonic beam.

The output signals from the transmission beamformer 606 are supplied to the plurality of ultrasonic transducers that constitute the transmission aperture as drive signals via a transmission/reception (T/R) switch circuit 608. The plurality of ultrasonic transducers supplied with the drive signals respectively generate ultrasound to form an ultrasonic beam to be transmitted in a predetermined direction by wave-front synthesis of the ultrasound. The transmitted ultrasonic beam is focused at a focal point located at a predetermined range. A portion consisting of the signal generating circuit 602, the transmission beamformer 606, the T/R switch circuit 608 and the ultrasonic probe 2 represents an embodiment of the ultrasound transmitting means of the present invention.

Echoes of the transmitted ultrasound are caught by a plurality of ultrasonic transducers that constitute a reception aperture in the ultrasonic probe 2. The plurality of echo signals caught by the plurality of ultrasonic transducers are input to a reception beamformer 610 via the T/R switch circuit 608. The reception beamformer 610 imparts delays corresponding to the direction of acoustic lines and the foci for the echo reception to the individual caught echo signals and sums up them to form a received echo signal matched to a predetermined acoustic line and focus.

A portion consisting of the ultrasonic probe 2, the T/R switch circuit 608 and the reception beamformer 610 represents an embodiment of the received signal generating means of the present invention. Moreover, a portion consisting of the signal generating circuit 602, the transmission beamformer 606, the T/R switch circuit 608, the reception beamformer 610 and the ultrasonic probe 2 represents an embodiment of the data collecting means of the present invention.

Figure 3:
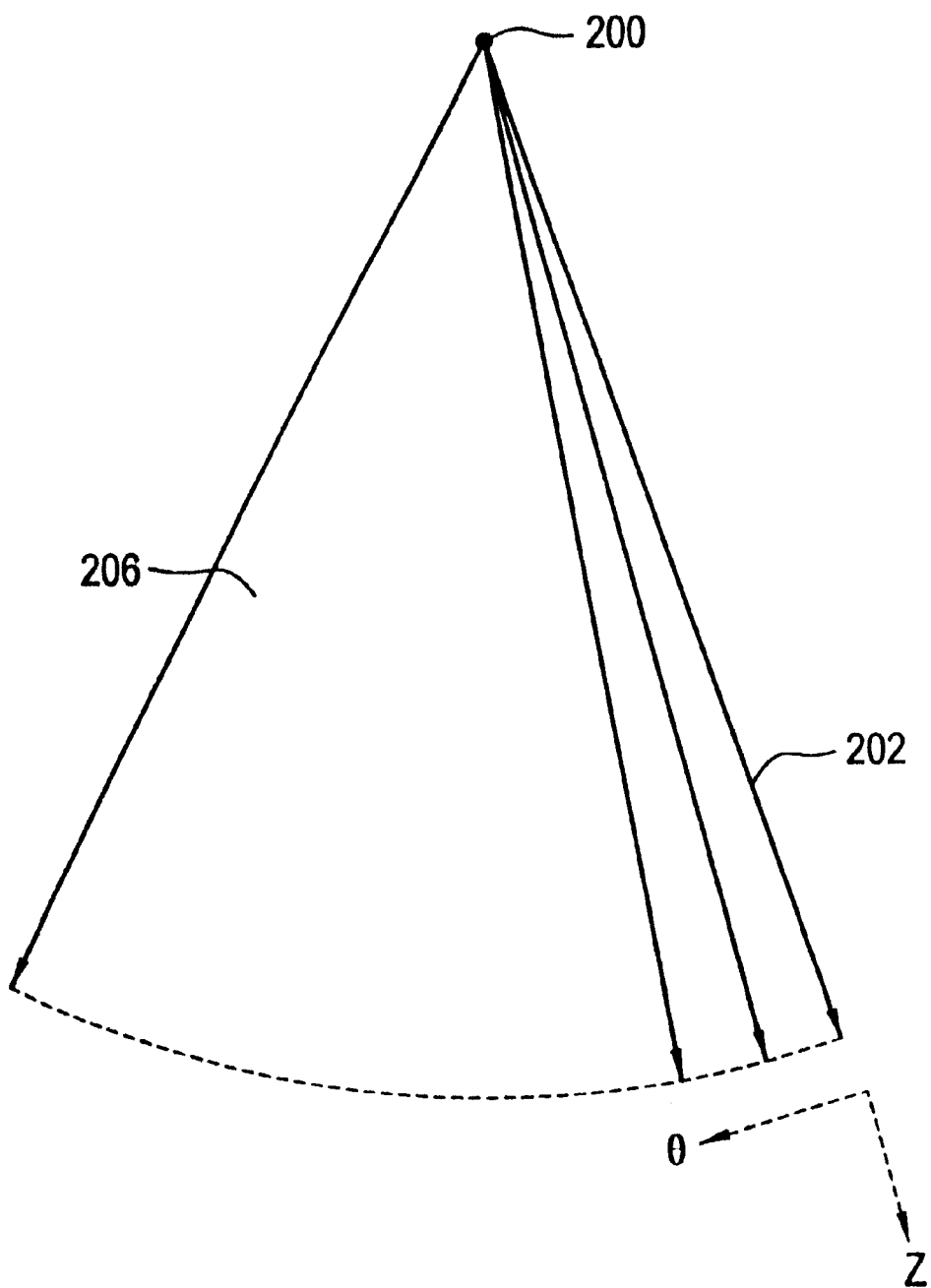
FIG. 3 schematically illustrates an acoustic line scan performed by the transceiver section shown in FIG. 2.

The transmission beamformer 606 performs an acoustic-line-sequential scan by sequentially switching the direction of the transmitted ultrasonic beam. The reception beamformer 610 performs an acoustic-line-sequential reception scan by sequentially switching the direction of the received acoustic line. Thus, the transceiver section 6 performs a scan as exemplarily shown in FIG. 3. Specifically, a fan-shaped two-dimensional region 206 is scanned in the θ-direction by an ultrasonic beam 202 extending from an emission point 200 in the z-direction, and a so-called sector scan is carried out.

Figure 4:
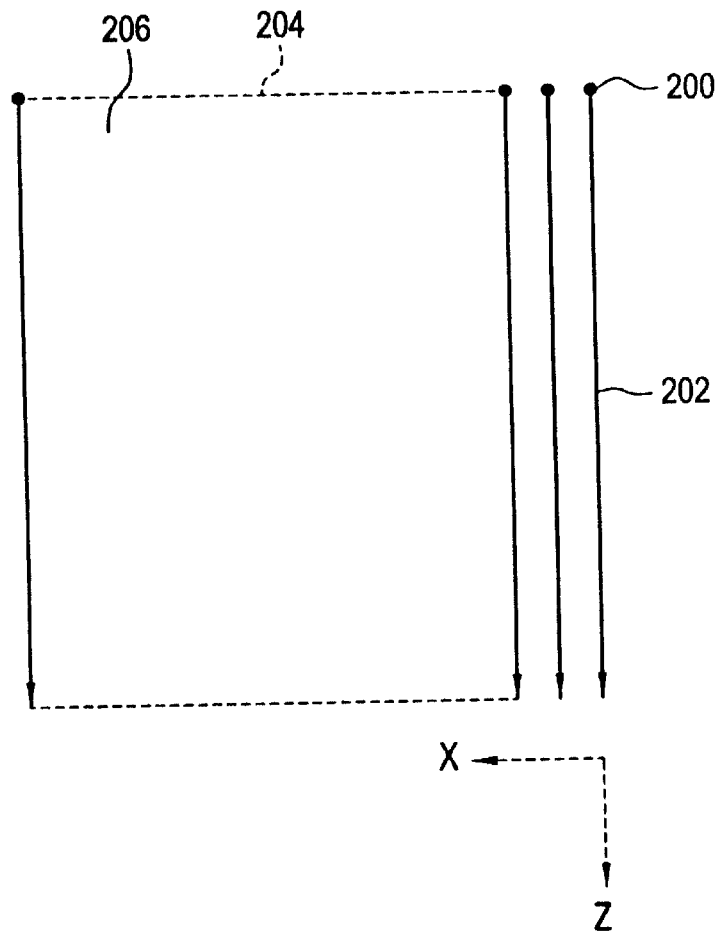
FIG. 4 schematically illustrates an acoustic line scan performed by the transceiver section shown in FIG. 2.

When the transmission and reception apertures are formed using part of the ultrasonic transducer array, a scan as exemplarily shown in FIG. 4 can be performed by sequentially shifting the apertures along the array. Specifically, a rectangular two-dimensional region 206 is scanned in the x-direction by translating an ultrasonic beam 202, which emanates from an emission point 200 in the z-direction, along a linear trajectory 204, and a so-called linear scan is carried out.

Figure 5:
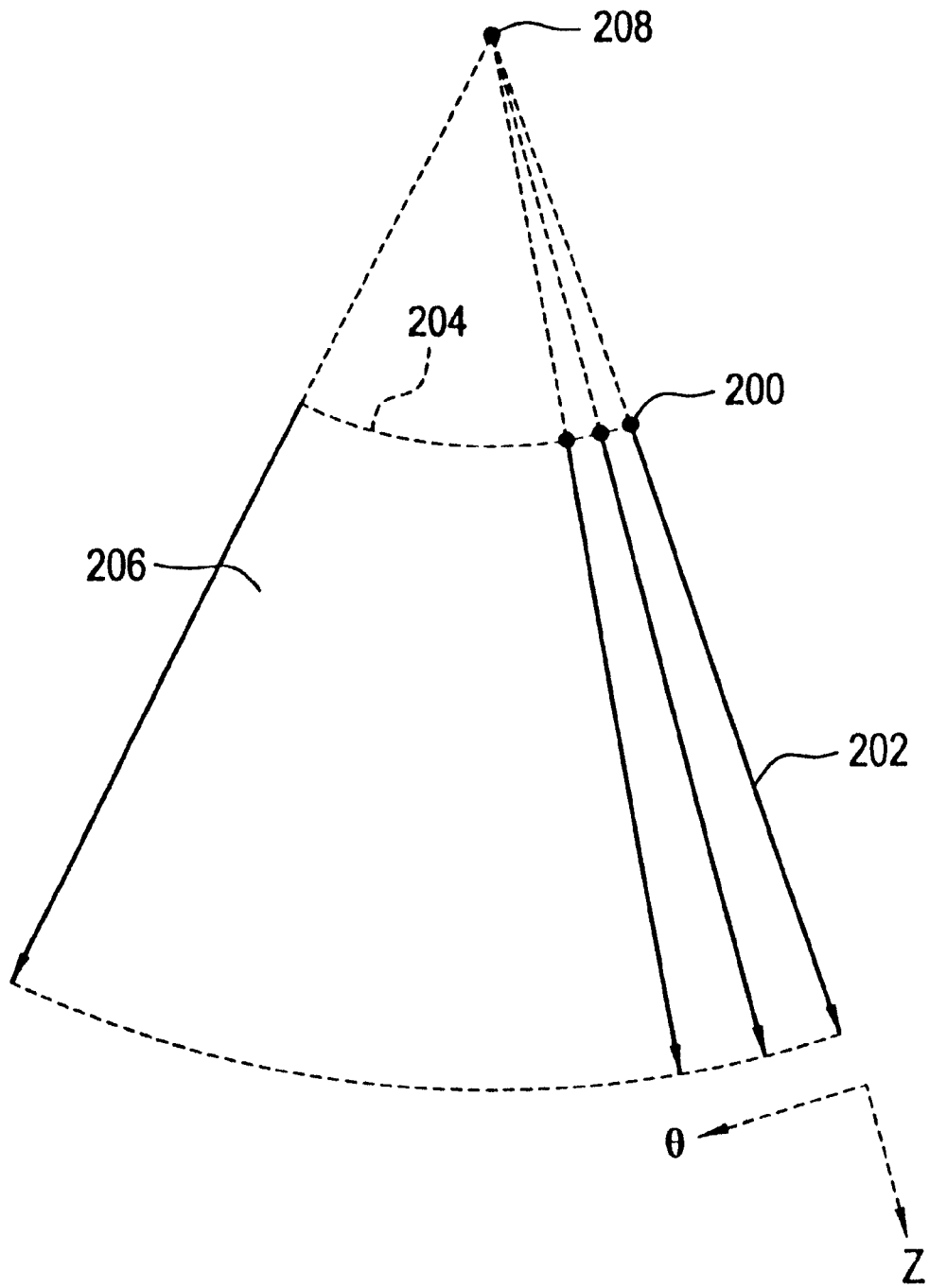
FIG. 5 schematically illustrates an acoustic line scan performed by the transceiver section shown in FIG. 2.

It will be easily recognized that when the ultrasonic transducer array is a so-called convex array, which is formed along an arc protruding toward the direction of ultrasound transmission, a partial fan-shaped two-dimensional region 206 can be scanned in the θ-direction by performing a signal operation similar to that for the linear scan and moving an emission point 200 of an ultrasonic beam 202 along an arc-like trajectory 204, and a so-called convex scan, as exemplarily shown in FIG. 5, is carried out.

Returning to FIG. 1, the transceiver section 6 is connected to a data processing section 8. The data processing section 8 is supplied with the received echo signals as digital data from the transceiver section 6. The data processing section 8 processes the supplied echo data to perform image production. The data processing section 8 represents an embodiment of the image producing means of the present invention and will be described in more detail later.

The data processing section 8 is connected with a display section 10, which is an embodiment of the image display means of the present invention. The display section 10 comprises, for example, a graphics display, and displays a visible image based on the image data supplied from the data processing section 8.

The transceiver section 6, the data processing section 8 and the display section 10 are connected to a controller section 12 for supplying control signals to these sections to control their operation. In addition, the controlled sections transmits status information signals and response signals etc. to the controller section 12. Ultrasonic imaging is performed under the control of the controller section 12.

The control section 12 is connected with an operating section 14 that is operated by a human operator inputting desired commands and information to the control section 12. The operating section 14 comprises an operating panel including, for example, a keyboard and other operating devices.

FIG. 6 shows a block diagram of a main portion of the data processing section 8. As shown, the data processing section 8 has a digital scan converter 802, which will be abbreviated as a DSC 802 hereinafter. The DSC 802 performs a scan conversion corresponding to the display operation of the display section 10 on the image data supplied from a preceding image generating circuit (not shown), and inputs the converted data into an overlay controller 804.

The image data may include, for example, B-mode image data, M-mode image data, point Doppler image data, color Doppler image data and power Doppler image data.

The overlay controller 804 combines the image data supplied from the DSC 802 with image data supplied from a graphics controller 806 and inputs the combined image data to a video processor 808 and a cine memory 820. The cine memory 820 represents the image saving means of the present invention.

The video processor 808 performs a predetermined process on the combined image data supplied, and inputs the data to the display section 10. The video processor 808 has an internal memory. The output signals from the video processor 808 are also input to an image recording device 822, which represents an embodiment of the image saving means of the present invention. For the image recording device 822, an image recording device such as a VTR (video tape recorder) or a DVD (digital versatile disk) device, or a hard copy creating device such as a video printer may be employed.

The graphics controller 806 also has an internal memory. The graphics controller 806 is supplied with graphical data from a CPU (central processing unit) 810. The CPU 810 is connected with a hard disk device (abbreviated as HD hereinafter) 812, a main memory (abbreviated as MM hereinafter) 814, an external input interface 816 and a recording medium reading device 818. The HD 812 stores programs and data for the CPU 810. The CPU 810 loads them on the MM 814 for execution.

The external input interface 816 is an interface through which an external image is input, and is, for example, a serial port compliant with a standard such as RS232C. However, the external input interface 816 is not limited to RS232C but may be one compliant with other standards such as SCSI, USB or IEEE 1394. The external input interface 816 represents an embodiment of the external image input means of the present invention. Through such an external input interface 816, an image is input from, for example, a digital still camera, a digital video camera or an image scanner.

The external input interface 816 may be one which is compliant with a LAN (local area network) such as Ethernet or Internet such as WWW (World Wide Web). This allows images and character information to be read out from networks. The term "image" as used hereinafter is to be construed as including character information.

The recording medium reading device 818 is, for example, an FD (flexible disk) device, an MO (magnetic optical disk) device or a DVD device, for reading out and inputting the image recorded on their respective recording media. Alternatively, the recording medium reading device 818 may be a reading device for a portable semiconductor memory such as a card-type flash memory. The recording medium reading device 818 represents an embodiment of the external image input means of the present invention.

The external image supplied via the external input interface 816 or the recording medium reading device 818 is stored in the HD 812 or the MM 814 and is input to the graphics controller 806 as graphical data via the CPU 810. The HD 812 represents an embodiment of the image saving means of the present invention. The MM 814 also represents an embodiment of the image saving means of the present invention.

As the external image, any image selected by the user of the present apparatus can be taken in unrestrictedly. Any kinds of image information can be taken in regardless of genre, and such image information may include, for example, a photograph of the face of the subject to be imaged, a photograph capturing the situation of imaging or a photograph of the face of the mother when a fetus is imaged, a predetermined background image imprinted with a logo mark of the user, a background image to the user's taste or an ornamental image, a document created by a word processing software or a spreadsheet software or an HTML (hyper text markup language) document or the like.

Now the operation of the present apparatus will be described. In the following description, it is assumed that an external image has been taken in via the external input interface 816 or the recording medium reading device 818 and stored in the HD 812 or the MM 814. The operator designs arrangement of the display screen of the display section 10 prior to imaging. The design of screen arrangement is executed by data processing by the CPU 810 based on the operation of the operating section 14. Thus, a display screen such as those shown in FIG. 7 (a) or (b) is constructed. A portion consisting of the operating section 14 and the CPU 810 represents an embodiment of the display area arranging means of the present invention.

Figure 7A:
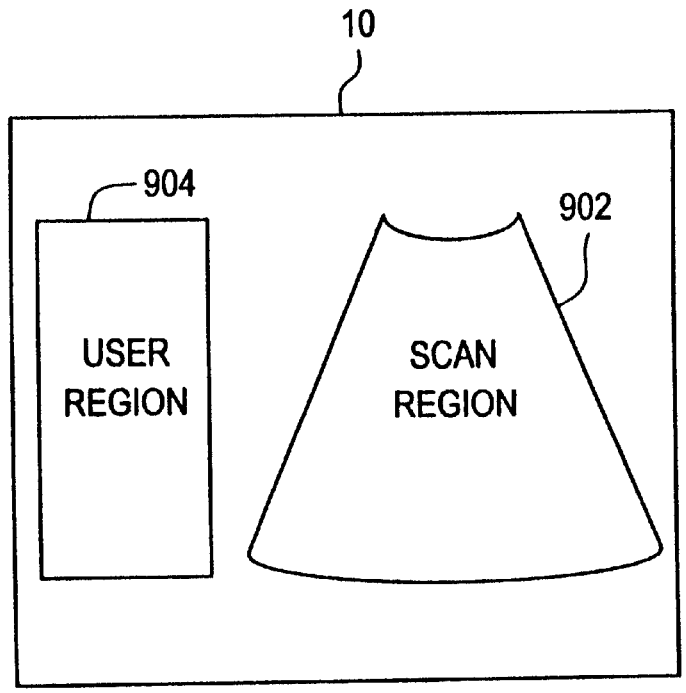
FIG. 7 is a schematic showing a display screen of a display section in the apparatus shown in FIG. 1.
Figure 7B:
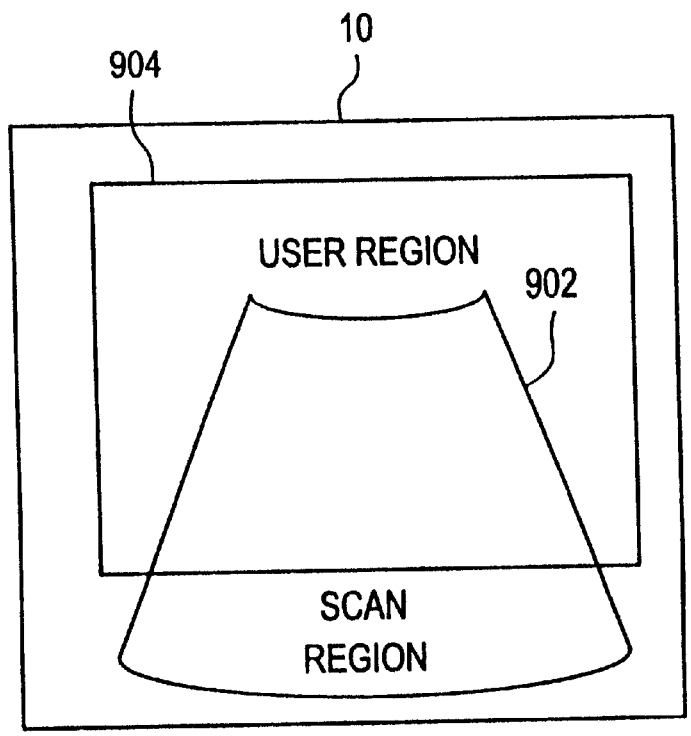

In FIG. 7 (a), the screen arrangement is such that a display segment for a captured image, i.e., a scan image 902 and a display segment for the external image, i.e., a user region 904 are disposed side by side. The user region 904 represents an embodiment of the display area open to a user of the present invention. In FIG. 7 (b), the screen arrangement is such that the scan image 902 and the user region 904 are partially overlapped with each other. It should be noted that in the overlapped portion, the underlying image can be viewed penetrating the overlying image.

The design of the display screen is not limited to the style as shown in FIG. 7, but may be any appropriate style according to the purpose of use. The size of the user region 904 may be changed appropriately. Moreover, multi-window display may be allowed, and in this case, the scan image 902 and the user region 904 may be displayed in the same window or in separate windows. Furthermore, a plurality of screen styles may be designed and saved in the HD 812 to allow the user to select an appropriate one from these styles for use.

The operator makes a desired external image read out from the HD 812 etc. for display in the user region 904 in such a styled screen. Then the operator puts the ultrasonic probe 2 against a desired site of the subject 100 and operates the operating section 14 to perform ultrasonic imaging. The imaging is performed under the control of the controller section 12 based on commands issued by the operator.

Then, the transceiver section 6 performs a convex scan, for example, as shown in FIG. 5. The data processing section 8 produces a B-mode image, for example, based on the received echo data, and combines the image with the external image from the graphics controller 806 by the overlay controller 804, processes the combined image by the video processor 808, and supplies the image to the display section 10. Thus, the scan image 902 is displayed on the display section 10 in the style shown in FIG. 7 (a) or (b).

It should be noted that an image to be displayed in the user region 904 may be a plurality of frames of images sequentially switched at appropriate times. This can be done by storing the plurality of frames of images in the memory in the graphics controller 806. The frame rate of the switching may be the same as or different from the frame rate of the scan image 902.

Thus, displaying an external image in the user region 904 along with the scan image 902 can enrich information and the utility of the present apparatus can be improved. In addition, an appropriate natural landscape etc. may be employed as the external image to make a preferable psychological effect on an observer by the impression of such an image.

The displayed images are saved in the image recording device 822 connected to the video processor 808. Moreover, the output data from the overlay controller 804 stored in the cine memory 820 can be used for later image playback. The contents of the cine memory 820 may be saved in an HD device, FD device, MO device, DVD device or the like (not shown). Furthermore, the contents of the memory of the video processor 808 may be saved in an HD device, FD device, MO device, DVD device or the like (not shown).

While the present invention has been described with reference to an ultrasonic imaging apparatus as a particular example, the invention is not limited to being practiced with the ultrasonic imaging apparatus but may apply to various medical imaging apparatuses such as an X-ray CT apparatus, a magnetic resonance imaging apparatus and an X-ray imaging apparatus, and the same effects can be obtained in any apparatus.

Many widely different embodiments of the invention may be configured without departing from the spirit and the scope of the present invention. It should be understood that the present invention is not limited to the specific embodiments described in the specification, except as defined in the appended claims.

What is claimed is:

1. A medical imaging method comprising the steps of:
   collecting imaging data from a part of a human subject;
   producing a main image of said part of said human subject based on said collected data;
   displaying said produced main image of said part of said human subject in a part of a display screen;
   providing external data for an external image of another subject other than said part of said human subject from which said imaging data was collected;
   concurrently displaying, under control of an operator, said external image of said other subject in another part of said display screen; and selectively controlling both said displaying step and said concurrently displaying step so that said part of said display screen and said other part of said display screen are selectively arranged to be at least partially overlapping of each other so that said main image and said external image are at least partially overlapped with the underlying image viewed penetrating the overlapped image.

2. The method of claim 1, wherein said collecting step comprises:

transmitting ultrasound to a human subject being examined; and generating received image data associated with said transmitted ultrasound reflected by said human subject.

3. The method of claim 1 or 2, further comprising the step of storing at least said external image of said other subject.

4. A medical imaging apparatus comprising:

means for collecting imaging data from a part of a human subject;

means for producing a main image of said part of said human subject based on said collected data;

first display means for displaying said produced main image of said part of said human subject in a part of said display screen;

means for providing external data for an external image of another subject other than said part of said human subject from which said data was collected;

second display means for concurrently displaying under manual control of an operator said external image of said other subject in another part of said display screen; and means for selectively controlling said first and second display means so that said part of said display screen and said other part of said display screen are selectively arranged to be at least partially overlapping of each other so that said main image and said external image are at least partially overlapping with the underlying image viewed penetrating the overlapping image.

5. The apparatus of claim 4, wherein said means for collecting data comprises:

means for transmitting ultrasound to a human subject; and means for generating received image data associated with said transmitted ultrasound reflected by said human subject.

6. The apparatus of claim 4 or 5, further comprising means for storing at least said external image displayed in said other part of said display screen.

7. The method of claim 1 or 2, wherein said external image is provided by a digital still camera, a digital video camera, or an image scanner.

8. The apparatus of claim 4 or 5, wherein said external image is provided by a digital still camera, a digital video camera, or an image scanner.

* * * * *